United States Patent [19]

Sauer

[11] 4,042,621
[45] Aug. 16, 1977

[54] OXIDATION OF N-SUBSTITUTED METHYLAMINES TO N-SUBSTITUTED FORMAMIDES

[75] Inventor: John Carl Sauer, Hockessin, Del.

[73] Assignee: E. I. Du Pont de Nemours and Company, Wilmington, Del.

[21] Appl. No.: 615,497

[22] Filed: Sept. 22, 1975

[51] Int. Cl.$^2$ ............................................ C07C 103/36
[52] U.S. Cl. .......................... 260/561 R; 260/239 B; 260/268 C; 260/293.86; 260/562 R; 260/562 P
[58] Field of Search ........... 260/562 R, 561 R, 562 P, 260/268 C, 293.86, 239 B

[56] References Cited

U.S. PATENT DOCUMENTS

| 2,793,211 | 5/1957 | LoCicero et al. | 260/562 R X |
| 3,483,210 | 12/1969 | Rosenblatt | 260/562 R X |
| 3,530,182 | 9/1970 | Haynes et al. | 260/562 R X |

OTHER PUBLICATIONS

Rosenblatt et al., Tetrahedron Letters, vol. 38, 4085 (1968).
Yoke et al., Inorganic Chem., 2, 1210-1216 (1963).

*Primary Examiner*—Helen M. S. Sneed
*Attorney, Agent, or Firm*—Anthony P. Mentis

[57] ABSTRACT

An N-substituted methylamine is reacted in a liquid homogeneous system with molecular oxygen in the presence of a soluble halide of certain metals to produce an N-substituted formamide. Exemplary is the reaction of trimethylamine with oxygen in the presence of cupric chloride to produce dimethylformamide.

24 Claims, No Drawings

OXIDATION OF N-SUBSTITUTED METHYLAMINES TO N-SUBSTITUTED FORMAMIDES

BACKGROUND OF THE INVENTION

1. Field of the Invention

This invention is the process of reacting an N-substituted methylamine with molecular oxygen in a homogeneous system containing a soluble, i.e., dissolved, metal halide catalyst to produce an N-substituted formamide. The starting amine compound can be secondary or tertiary and can be a monoamine or diamine, and the diamine can be mixed, that is, contain a secondary and tertiary amine group in the molecule.

2. Description of Prior Art

U.S. Pat. No. 3,483,210 to Rosenblatt and Davis discloses the oxidation of the methyl group of a tertiary N-methyl-amine to a formyl group by the use of oxygen at atmospheric pressure with the amine in liquid phase in the presence of a heterogeneous (insoluble) catalyst of the platinum metal group.

SUMMARY OF THE INVENTION

The invention is the process of reacting in a liquid homogeneous system molecular oxygen with a compound of the formula

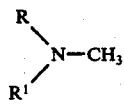

wherein
R is alkyl of 1–8 carbons, aryl of 6–10 carbons, aralkyl of 7–10 carbons or alkaryl of 7–10 carbons;
$R^1$ is aryl of 6–10 carbons, aralkyl of 7–10 carbons, alkaryl of 7–10 carbons, alkyl of 1–8 carbons or such alkyl containing $-N(CH_3)R^2$
in which $R^2$ is hydrogen, alkyl of 1–8 carbons, aryl of 6–10 carbons, aralkyl of 7–10 carbons or alkaryl of 7–10 carbons;
with the provisos that
R and $R^1$ can be joined together to form an alkylene or azaalkylene group of 3–8 carbons; and
when R is alkyl or aralkyl, $R^1$ can be hydrogen; in the presence of a catalytically effective amount of a soluble chloride, bromide or iodide of a metal selected from the group consisting of cobalt, copper, gold, iron, manganese, mercury, nickel, palladium, platinum, rhenium, silver and zinc; at a temperature in the range 25°–160° C and at an oxygen pressure in the range atmospheric to 500 pounds per square inch gauge; and recovering an N-substituted formamide of the formula

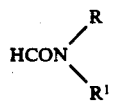

The reaction may be generally represented as:

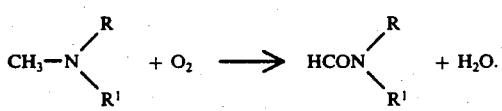

The formed formamide can be isolated from the reaction by any conventional means. When $R^1$ is an amino-substituted alkyl group as indicated above it is evident that bisformamides can be produced. Presently preferred is the reaction of trimethylamine with oxygen in the presence of cupric chloride to produce dimethylformamide.

"Aryl" means a monovalent radical derived by removal of a hydrogen atom from an aromatic hydrocarbon containing no aliphatic substituents. Included are phenyl, naphthyl and biphenylyl, etc.

"Aralkyl" means an alkyl group substituted with an aryl group and includes benzyl, naphthylmethyl, phenethyl and the like.

"Alkaryl" is an aryl group containing one or more alkyl substituents, as for example, tolyl, butylphenyl, trimethylphenyl and so on.

The preferred amine reactants are mono(tertiary amines), i.e., those in which $R^1$ is other than hydrogen and does not bear a substituted amino substituent. Copper halides are the preferred catalysts, and for all metals the chlorides are the preferred halides.

Oxygen can be used pure or in the form of air. If desired, it can also be used diluted with an inert gas such as helium or argon, but no advantage results. Although the process proceeds with oxygen at atmospheric pressure, for practical purposes it is desirable to use an oxygen pressure of at least about 80 psig, the preferred range being about 80–300 psig. Partial oxygen pressures higher than about 500 psig can be used, but no advantage results. The foregoing values refer to the pressure of oxygen alone; thus, when air is used the figure will be increased about fivefold, i.e., the maximum pressure will be about 2500 psig and the preferred range will be about 400–1500 psig. As will be obvious to one skilled in the art, the amine reactant and the solvent, if one is used, will make minor contributions to the total pressure.

It is not necessary to use a solvent as a medium for the reaction but its use is advantageous in helping to dissolve the catalyst and/or in moderating the exothermic reaction that sometimes takes place. Organic donor solvents that do not react with the amine or with oxygen under the reaction conditions are operable and include amides, such as methylformamide, dimethylformamide, dimethylacetamide, and hexamethylphosphoramide; alkanenitriles such as acetonitrile and propionitrile; alkanols such as methanol, ethanol, isopropyl alcohol and butyl alcohol; and sulfoxides such as dimethyl sulfoxide. Dimethylformamide is a preferred solvent. Hexamethylphosphoramide has been described in Chemical and Engineering News, page 17, Sept. 29, 1975, as being a possible carcinogen when inhaled. Due care should be taken when using this material.

An advantageous method of operating is to carry out the process in the presence of a preformed quantity of the desired product as solvent. In this way the necessity of separating the product from a disparate solvent is avoided. It is particularly preferred to oxidize trimethylamine in the presence of a preformed amount of dimethylformamide, which is the product produced in the reaction.

Whether or not a solvent is used, the catalyst dissolves in the liquid reaction medium under reaction conditions, usually completely but always to a significant extent, i.e., enough to provide a catalytic effect. The process thus involves a homogeneous liquid-phase catalytic reaction.

The amount of catalyst can be varied over wide limits so long as it is present in a catalytically effective amount i.e., an amount which produces a significant quantity of the desired product under the reaction conditions used. Usually between 0.1 g and 10 g of catalyst per mole of amine is used. Higher amounts can be used, but no advantage results. The preferred range is between about 0.2 g and 6 g of catalyst per mole of amine. Amounts of catalyst lower than 0.1 g per mole of amine can be used as long as they provide a catalytic effect. Either anhydrous or hydrated metal halides can be used. Although large amounts of water may inhibit the reaction the amount of water of hydration in a catalytic amount of hydrated metal halide is too small to have a significant effect.

The temperature will depend on the particular catalyst and also on the oxygen pressure. Temperatures in the range about 25° to 160° C are operable. Reaction is relatively slow in the lower part of this range, and above about 160° C overoxidation tends to take place. The preferred range is about 90° to 140° C. With a relatively active catalyst like cupric chloride, the pressure should not be over about 300 psig at 105°–110° C, in order to avoid vigorous exothermic reaction leading to overoxidation.

Water is formed in the process of the invention as a by-product. As noted above minor amounts of water do not affect the process; hydrated catalysts can be used, and there is no need to use anhydrous solvents. The reaction appears to slow down when the water content of the mixture reaches about 15-25%. It is therefore advantageous to operate in such a manner that the water formed is continuously removed from the reaction zone. One such method is a continuous process.

The progress of the reaction can be followed by observing the pressure drop as oxygen is consumed. The product can be isolated by conventional procedures such as distillation, gas chromatography, and the like.

The foregoing discussion of process variables applies to a batch process, as in a shaker tube or an autoclave equipped with a stirrer. The process can also be carried out in a continuous manner whereby higher temperatures and pressures and shorter reaction time can be used.

SPECIFIC EMBODIMENTS OF THE INVENTION

The following examples are illustrative of how the invention can be practiced. Unless otherwise stated, all pressures are psig, and all parts and percentages are by weight and all temperatures are Centigrade.

% Conversion is defined as $$100 \times \frac{[(\text{grams amine charged}) - (\text{grams amine recovered})]}{\text{grams amine charged}}$$

% Yield is defined as $$100 \times \frac{(\text{moles formamide formed})}{(\text{moles amine charged}) - (\text{moles amine recovered})}$$

EXAMPLE 1

A. To a tared 400-ml stainless-steel-lined shaker tube was added 40.0 g of dimethylformamide (DMF) and 1.5 g of cupric chloride dihydrate, $CuCl_2 \cdot 2H_2O$. The tube was cooled to about $-78°$ C in a mixture of solid carbon dioxide and acetone and evacuated, and 59.5 g of trimethylamine (1.0 mole) was added. The tube was placed in a heater and an oxygen line was attached. The oxygen line was connected to a gauge which had been previously calibrated to measure the amounts of oxygen injected into the reactor tube in terms of moles of oxygen. Shaking of the tube and its contents was started. Upon reaching room temperature the tube containing the DMF and dissolved $CuCl_2$ was pressured with oxygen to 150 psi. On further heating the tube to 103° C, a vigorous reaction took place as measured by an exotherm to 145° C and a drop in pressure from 285 psi to 180 psi. The tube was repressured an additional five times during 1.5 hours with pressures ranging from 155 psi to 330 psi; in each case an exotherm occurred during the addition of more oxygen. After 2 hours, a total of 0.72 mole of oxygen had been injected. The tube was cooled to room temperature and weighed again. The remaining gases, including part of the unreacted trimethylamine, were slowly vented through a trap containing 400 ml of 1.0 N hydrochloric acid. The tube was weighed again, cooled to about $-78°$ C, and quickly opened, and the contents were poured into a tared bottle chilled to about $-78°$ C, except for an aliquot (6.0 g), which was poured directly into 50 ml of 1 N hydrochloric acid. The weight of the reaction mixture (123.0 g) was determined by subtracting the tare of the tube from the weight of the tube and contents after bleed-down. The weights of the unreacted trimethylamine were determined by titration of the aliquot and the contents of the trap with 1.0 N sodium hydroxide.

The total unreacted trimethylamine was 24.1 g, and by subtraction from the 59.5-g charge, the amount of reacted trimethylamine came to 35.4 g. The conversion of trimethylamine was about 60%. The yield was determined by measuring the dimethylformamide content by gas chromatography. The reaction mixture contained 62.1% dimethylformamide (76.4 g) of which 36.4 g was formed in the reaction. This corresponds to a yield of 83.3% based on trimethylamine consumed. The amount of amine left in the reaction mixture at the conclusion of the process can also be determined by gas chromatography.

B. By comparative experiments, it was shown that cupric chloride dihydrate dissolved in an organic donor solvent was markedly superior to insoluble platinum-on-carbon catalysts, which are typical of the prior art. These experiments are summarized in Table I. In each run 59 g of trimethylamine and 40 g of dimethylformamide were charged, as in Example 1, and the procedure was essentially that of Example 1.

TABLE I

| Ex. | Catalyst - grams | Solvent | Temp. | Pressure psig | Time Hrs:Min | % Conv. | % Yield |
|---|---|---|---|---|---|---|---|
| 1 B-1 | 0.7 $CuCl_2 \cdot 2H_2O$ (0.26 Cu) | DMF | 109–112 | 150–225 | 0:20 | 34.5 | 100 |
| 1 B-2 | 0.7 $CuCl_2 \cdot 2H_2O$ (0.26 Cu) | Ethanol | 110 | 165–230 | 0:20 | 6.6 | 89.4 |
| 1 B-3 (1), (2) | 2.6 10% Pt on C (0.26 Pt) | Benzene | 110 | 175–225 | 0:20 | 1.6[3] | high |
| 1 B-4 (1) | 4.0 5% Pt on C (0.2 Pt) | DMF | 110 | 200–400 | 2:00 | 33 | 86.3 |

TABLE I-continued

| Ex. | Catalyst - grams | Solvent | Temp. | Pressure psig | Time Hrs:Min | % Conv. | % Yield |
|---|---|---|---|---|---|---|---|
| 1 B-5 (1) | 1.34 15% Pt on C (0.2 Pt) | DMF | 125 | 230-240 | 2:00 | 47 | 76 |

(1) - Prior art catalyst
(2) - 60 g trimethylamine used
(3) - very low; determined from amount of DMF produced The data in the table show that the three runs using heterogeneous catalysts of the prior art are not as efficient as the process of the invention. The shorter times under relatively mild conditions afforded by the process of the present invention make possible a cleaner reaction with less overoxidation and fewer oxidative side reactions. In addition, the homogeneous nature of the present process permits the catalyst to be recycled after most of the solvent is removed by distillation; filtration steps with concomitant losses are thereby avoided.

By essentially the procedure of Example 1, a number of other oxidations of trimethylamine to dimethylformamide were carried out by the process of the invention. The results are summarized in Table II.

| Composition of Starting Mixture | Composition of Product Mixture |
|---|---|
| 15.5%* trimethylamine | 6.1% trimethylamine |
| 84.4% dimethylformamide | 93.3% dimethylformamide |
|  | 0.6% water |

*By gas chromatography, compared with 16.5% calculated.

EXAMPLE 27

By essentially the procedure of Example 1, a tube was charged with 20 g of N-methylpiperidine, 20 g of dimethylformamide, and 1 g of cupric chloride dihydrate. The reaction was run at 110°-112° C for 2 hr, during

TABLE II

| Example | Grams catalyst | Grams trimethyl-amine | Grams solvent | Temp, °C | Press. psig | Time hr:min | % Conv | % Yield | Remarks |
|---|---|---|---|---|---|---|---|---|---|
| 2 | 0.7 CuCl$_2$ · 2H$_2$O | 59.2 | 40 DMF$^1$ | 109-112 | 160-225 | 0:20 | 34.5 | 100.0 | |
| 3 | 0.2 CuCl$_2$ · 2H$_2$O | 59.5 | " | 104-110 | 180-255 | 2:00 | 35.0 | 98.3 | |
| 4 | 1.5 CuCl$_2$ · 2H$_2$O | 10 | 20 DMF$^1$ | 105-107 | 225-255 | 2:00 | 36.0 | 99.9 | O$_2$ as air |
| 5 | 0.7 CuCl$_2$ · 2H$_2$O | 59 | 5 DMF$^1$ | 127-140 | 260-360 | 0:31 | 47.0 | 56.8 | |
| 6 | 2.0 CuCl$_2$ · 2H$_2$O | " | none | 105-130 | 300-450 | 1:36 | 31.0 | 95.5 | |
| 7 | 0.7 CuCl$_2$ · 2H$_2$O | " | 40 MMF$^2$ | 105 | 150-250 | 0:73 | 35.6 | Calc'd ≧100 | |
| 8 | 1.0 CuCl$_2$ · 2H$_2$O | " | 40 CH$_3$CN | 105-111 | 150-250 | 2:00 | 36.6 | 76.8 | |
| 9 | 1.0 Cu$_2$Cl$_2$ | " | 40 DMF | 106-121 | 160-250 | 0:27 | 41.2 | 86.7 | |
| 10 | 1.0 CuBr$_2$ | " | " | 105-123 | 170-250 | 0:27 | 42.1 | 87.0 | |
| 11 | 1.0 Cu$_2$I$_2$ | " | " | 104-115 | 150-200 | 0:44 | 59.0 | 100.0 | |
| 12 | 1.5 FeCl$_3$ · 6H$_2$O | " | " | 135 | 300-400 | 2:00 | 37.9 | 83.1 | |
| 13 | 1.5 NiCl$_2$ · 6H$_2$O | 58 | " | 136-140 | 280-400 | 2:00 | 50.9 | 97.2 | |
| 14 | 1.5 CoBr$_2$ · 6H$_2$O | 60.4 | 40 DMF | 103-104 | 245-300 | 2:00 | 29.4 | 71.0 | |
| 15 | 1.5 CoCl$_2$ · 6H$_2$O | 59 | " | 120-122 | 230-355 | 2:00 | 20.6 | 76.4 | |
| 16 | 2.0 AgCl | " | " | 150 | 350-400 | 2:00 | 6.7 | 59.7 | |
| 17 | 1.0 AuCl$_3$ | " | " | 130 | 280-400 | 2:00 | 47.6 | 79.0 | |
| 18 | 1.0 ZnCl$_2$ | " | " | 140 | 300-400 | 2:00 | 20.9 | 100.0 | |
| 19 | 1.5 HgCl$_2$ | " | " | 140 | 300-500 | 3:18 | 32.9 | 91.5 | |
| 20 | 1.5 MnCl$_2$ · 4H$_2$O | " | " | 135 | 275-285 | 2:00 | 5.2 | Low | |
| 21 | 1.0 ReCl$_3$ | " | " | 135-140 | 325-400 | 2:00 | 10.8 | 35.2 | |
| 22 | 1.0 PdCl$_2$ | " | " | 145-146 | 300-355 | 4:40 | 26.0 | 84 | |
| 23 | 0.52 PdCl$_2$ | 20 | " | 125 | 210-300 | 16:50 | 76.0 | 64 | |
| 24 | 0.78 PtCl$_2$ | 20 | " | 125 | 250-300 | 17:35 | 55.9 | 72.8 | |
| 25 | 1.00 CuCl$_2$ · 2H$_2$O | 59 | 40 Ethanol | 110-116 | 120-200 | 3:30 | 58 | 93 | |

1) DMF is dimethylformamide
2) MMF is monomethylformamide

In each of Examples 2-8 the run was shut down after about 0.8 mole of oxygen per mole of trimethylamine had been consumed, as indicated by pressure drop. Examples 9-25 illustrate the use of other soluble metal halides as catalysts.

EXAMPLE 26

A 200-ml bottle was charged with 2.0 g of cupric chloride dihydrate and 112.7 g of a dimethylformamide solution containing 16.5% trimethylamine. The bottle was fitted with a serum stopper, and a slow stream of O$_2$ was swept through the bottle, replacing the air. The reaction mixture was stirred magnetically at room temperature and atmospheric pressure for 70.5 hours, during which time oxygen was swept over the reaction mixture nine times to insure an adequate amount of oxygen. The reaction mixture was analyzed just prior to starting the reaction and at the termination of the reaction. The results shown below indicate that oxidation of trimethylamine to dimethylformamide proceeded at room temperature and atmospheric pressure.

which time oxygen was injected incrementally at 90-300 psi. The total amount of oxygen injected was 0.26 mole. Analysis by combined gas chromatography and mass spectroscopy (GC/MS) showed an 86.5% conversion of N-methylpiperidine and a 15.9% yield of 1-piperidinecarboxaldehyde, also known as N-formylpiperidine or pentamethyleneformamide.

EXAMPLE 28

By essentially the procedure of Example 1, a tube was charged with 20 g of dimethylaniline, 20 g of dimethylformamide, and 1.0 g of cupric chloride dihydrate. The reaction was run at 114°-115° C for one hour while oxygen was injected incrementally at 200-400 psi. The oxygen absorption was about 0.12 mole. Analysis of the reaction mixture by GC/MS showed a 94.5% conversion of dimethylaniline and a 15.4% yield of N-methyl-N-phenylformamide.

EXAMPLE 29

By essentially the procedure of Example 1, a tube was charged with 20 g of N,N,N',N'-tetramethylethylenediamine, 20 g of dimethylformamide, and 1.0 g of cupric chloride dihydrate. The reaction was run at 105°-123° C for five hours while oxygen (0.4 mole) was injected incrementally. Analysis of GC/MS showed a 29.4% conversion of the starting diamine, a 2.4% yield of N,N'-ethylenebis(N-methylformamide), and a 6% yield of N-(2-dimethylaminoethyl)-N-methylformamide.

EXAMPLE 30

By essentially the procedure of Example 1, a tube was charged with 45 g of dimethylamine, 20 g of dimethylformamide, and 1.5 g of cupric chloride dihydrate. The reaction was run at 110°-125° C for 50 min at a pressure of 120-250 psi. The oxygen absorption was about 0.8 mole. Analysis of the product by gas chromatography showed a 29.3% conversion of dimethylamine and a 46.1% yield of monomethylformamide.

By a similar procedure with acetonitrile as solvent, a 12.7% yield of monomethylformamide was obtained.

EXAMPLE 31

By essentially the procedure of Example 1, a tube was charged with 20 g of N-methylpiperazine, 1.0 g of $CuCl_2 \cdot 2H_2O$ and 20 g of acetonitrile. The reaction was run at 108°-112° C/200-360 psi/50 min. The oxygen injected into the tube amounted to 0.25 mole. GC/MS showed a 93.3% conversion of N-methylpiperazine and 2.7% yield of 1-piperazinecarboxaldehyde, also known as N-formylpiperazine or 3-azapentamethyleneformamide.

EXAMPLE 32

By essentially the procedure of Example 1, a tube was charged with 20 g of diethylmethylamine, 20 g of acetonitrile, and 1.5 g of $CuCl_2 \cdot 2H_2O$. The reaction was run at 106°-120° C for 2 hr during which oxygen (0.58 mole) was injected incrementally at 100-250 psi. GC/MS analysis of the product showed a 73.3% conversion of diethylmethylamine and a 17.5% yield of diethylformamide.

EXAMPLE 33

By essentially the procedure outlined in Example 1, a tube was charged with 25 g of benzyldimethylamine, 20 g of acetonitrile, and 1.0 g of $CuCl_2 \cdot 2H_2O$. The reaction was run at 106°-110° C for 2 hr during which oxygen (0.17 mole) was injected incrementally at 50-100 psi. GC/MS analysis showed a 94% conversion of benzyldimethylamine and a 31.6% yield of benzylmethylformamide.

EXAMPLE 34

By essentially the procedure of Example 1, a tube was charged with 40 g of methyldioctylamine and 1.0 g of $CuCl_2 \cdot 2H_2O$. The reaction was run at 109°-120° C for 25 min while oxygen (0.2 mole) was injected incrementally at 160-275 psi. GC/MS analysis showed a 72.0% conversion of methyldioctylamine and a 4.5% yield of dioctylformamide.

EXAMPLE 35

By essentially the procedure of Example 1, a tube was charged with 40 g of methyldiphenylamine and 2.0 g of $CuCl_2 \cdot 2H_2O$. The reaction was run at 115°-125° C for 2 hr at 290-400 psi. About 0.1 mole of oxygen was injected incrementally. GC/MS analysis showed a 98.6% conversion of methyldiphenylamine and a 43.3% yield of diphenylformamide.

EXAMPLE 36

By essentially the procedure of Example 1, a shaker tube was charged with 40 g of dimethylformamide, 1.0 g of cupric chloride dihydrate, and 11.0 g of trimethylamine. The reaction was run at 105°-116° C, oxygen being injected incrementally at 50-150 psi, for 18 minutes, by which time absorption of oxygen had essentially ceased. About 0.2 mole of oxygen was injected. Analysis as in Example 1 showed a 99% conversion of dimethylamine and 95.5% yield of dimethylformamide.

The calculated total water content of the final mixture, including the water of hydration in the catalyst and the water formed in the oxidation, was about 6.2%. The results of this example show that at this level of water and below, trimethylamine is converted rapidly and essentially completely to dimethylformamide without inhibition.

EXAMPLE 37

By essentially the procedure of Example 1, a shaker tube was charged with 80 g of dimethylformamide, 15 g of cupric chloride dihydrate, and 59 g of trimethylamine. The reaction was run at 97°-110° C, oxygen being injected incrementally at 45-200 psi, for 55 minutes, by which time absorption had essentially ceased. About 2.0 moles of oxygen was injected. Analysis indicated an 84-85% conversion of trimethylamine and a 92.7% yield of dimethylformamide. No trimethylamine was volatilized during bleed-off of the tube, but titration of an aliquot of the residual reaction mixture showed 9.2 g of unreacted trimethylamine to be present. This reaction mixture was distilled at atmospheric pressure until about 75 g of distillate, boiling at 99°-150° C, had been collected. The distillate contained essentially all the water and unreacted trimethylamine present in the reaction mixture. The undistilled liquid weighed 109.2 g and consisted essentially of dimethylformamide and anhydrous cupric chloride. It was charged to a shaker tube, and 11 g of trimethylamine was added, to slightly more than replace the amount of this reactant removed by distillation. This mixture was then reacted as before with oxygen at 110°-115° C and 20-250 psi for 35 minutes, by which time absorption had essentially ceased. Analysis showed no unreacted trimethylamine remaining in the reaction mixture. The overall conversion of trimethylamine was 100%, and the yield of dimethylformamide was 87%.

The results of this example show that the catalyst can be re-used without isolation, and that the inhibiting effect of water can be overcome by removing water from the reaction mixture as it is formed.

Other N-methylamines can be converted to the corresponding formamides by the process of the invention, as illustrated in the following table.

Table III

| Amine Reactant | Formamide Produced |
| --- | --- |
| N-methylpyrrolidine | tetramethyleneformamide |
| N-methylhexamethylenimine | hexamethyleneformamide |
| dimethyl(1-naphthyl)amine | N-methyl-N-(1-naphthyl)-formamide |
| N,N'-dimethyltetramethylene-diamine | N-(4-methylaminobutyl)-N-methylformamide tetramethylenebis(N-methyl- |

Table III-continued

| Amine Reactant | Formamide Produced |
|---|---|
|  | formamide) |
| hexylmethylamine | hexylmethylformamide |
| N,N-dimethylphenethylamine | N-methyl-N-phenethyl-formamide |
| 3-ethylphenyldimethylamine | 3-ethylphenyl(methyl)-formamide |
| methyldi(p-tolyl)amine | di(p-tolyl)formamide |

I claim:

1. The process of reacting in a liquid homogeneous system molecular oxygen with a compound of the formula

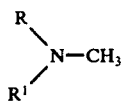

wherein
R is alkyl of 1-8 carbons, aryl of 6-10 carbons, aralkyl of 7-10 carbons or alkaryl of 7-10 carbons;
$R^1$ is aryl of 6-10 carbons, aralkyl of 7-10 carbons, alkaryl of 7-10 carbons, alkyl of 1-8 carbons or such alkyl containing $-N(CH_3)R^2$
in which $R^2$ is hydrogen, alkyl of 1-8 carbons, aryl of 6-10 carbons, aralkyl of 7-10 carbons or alkaryl of 7-10 carbons;
with the provisos that
R and $R^1$ can be joined together to form an alkylene or azaalkylene group of 3-8 carbons; and
when R is alkyl or aralkyl, $R^1$ can be hydrogen; in the presence of a catalytically effective amount of a soluble chloride, bromide or iodide of a metal selected from the group consisting of cobalt, copper, gold, iron, manganese, mercury, nickel, palladium, platinum, rhenium, silver and zinc; at a temperature in the range 25°-160° C and at an oxygen pressure in the range atmospheric to 500 pounds per square inch gauge; and recovering an N-substituted formamide of the formula

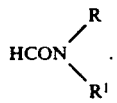

2. The process of claim 1 carried out in the presence of an organic donor solvent.

3. The process of claim 2 in which the solvent is an amide.

4. The process of claim 2 in which the solvent is dimethylformamide.

5. The process of claim 2 in which the solvent is ethanol.

6. The process of claim 2 in which the solvent is a preformed amount of the desired product.

7. The process of claim 1 in which the pressure is at least 80 psig.

8. The process of claim 1 in which the temperature range is 90° to 140° C.

9. The process of claim 1 in which the amine reactant is trimethylamine.

10. The process of claim 1 in which the metal constituent of the catalyst is cobalt.

11. The process of claim 1 in which the metal constituent of the catalyst is copper.

12. The process of claim 1 in which the metal constituent of the catalyst is gold.

13. The process of claim 1 in which the metal constituent of the catalyst is iron.

14. The process of claim 1 in which the metal constituent of the catalyst is manganese.

15. The process of claim 1 in which the metal constituent of the catalyst is mercury.

16. The process of claim 1 in which the metal constituent of the catalyst is nickel.

17. The process of claim 1 in which the metal constituent of the catalyst is palladium.

18. The process of claim 1 in which the metal constituent of the catalyst is platinum.

19. The process of claim 1 in which the metal constituent of the catalyst is rhenium.

20. The process of claim 1 in which the metal constituent of the catalyst is silver.

21. The process of claim 1 in which the metal constituent of the catalyst is zinc.

22. The process of claim 1 in which the catalyst is a chloride.

23. The process of claim 1 in which the catalyst is cupric chloride.

24. The process of claim 2 in which the starting compound is trimethylamine, the catalyst is cupric chloride, the solvent is dimethylformamide and the product recovered is dimethylformamide.

* * * * *